(12) United States Patent
Smith

(10) Patent No.: US 12,168,025 B2
(45) Date of Patent: *Dec. 17, 2024

(54) TRACE ELEMENTS

(71) Applicant: Warburton Technology Limited, Dublin (IE)

(72) Inventor: William Alfred Smith, Dublin (IE)

(73) Assignee: Warburton Technology Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 17/167,265

(22) Filed: Feb. 4, 2021

(65) Prior Publication Data

US 2021/0161953 A1   Jun. 3, 2021

Related U.S. Application Data

(60) Continuation of application No. 16/429,685, filed on Jun. 3, 2019, now Pat. No. 11,000,544, which is a continuation of application No. 15/968,866, filed on May 2, 2018, now Pat. No. 10,350,241, which is a continuation of application No. 15/660,439, filed on Jul. 26, 2017, now abandoned, which is a division of application No. 13/130,336, filed as application No. PCT/IB2009/055402 on Nov. 30, 2009, now Pat. No. 9,750,764.

(30) Foreign Application Priority Data

Dec. 9, 2008 (ZA) ................... 200810426

(51) Int. Cl.
| | | |
|---|---|---|
| *A61K 33/34* | (2006.01) | |
| *A23K 20/20* | (2016.01) | |
| *A23K 50/10* | (2016.01) | |
| *A61K 33/04* | (2006.01) | |
| *A61K 33/18* | (2006.01) | |
| *A61K 33/24* | (2019.01) | |
| *A61K 33/30* | (2006.01) | |
| *A61K 33/32* | (2006.01) | |
| *A61K 45/06* | (2006.01) | |

(52) U.S. Cl.
CPC ............. *A61K 33/34* (2013.01); *A23K 20/30* (2016.05); *A23K 50/10* (2016.05); *A61K 33/04* (2013.01); *A61K 33/18* (2013.01); *A61K 33/24* (2013.01); *A61K 33/30* (2013.01); *A61K 33/32* (2013.01); *A61K 45/06* (2013.01); *A23V 2002/00* (2013.01)

(58) Field of Classification Search
CPC .......... A61K 33/30; A61K 33/34; A61K 9/08; A61K 33/32

See application file for complete search history.

(56) References Cited

U.S. PATENT DOCUMENTS

| | | | | |
|---|---|---|---|---|
| 3,923,982 A | * | 12/1975 | Lamand ............... | A61K 9/0019 424/643 |
| 4,335,116 A | | 6/1982 | Howard | |
| 4,423,012 A | * | 12/1983 | Reynolds .............. | C22B 3/3846 205/605 |
| 5,372,822 A | * | 12/1994 | Fahim .................... | A61P 15/00 424/643 |
| 6,872,723 B2 | | 3/2005 | Frijlink | |
| 7,285,292 B2 | | 10/2007 | Laurie et al. | |
| 8,231,910 B2 | | 7/2012 | Laurie et al. | |
| 2004/0052872 A1 | * | 3/2004 | Ionascu .................. | A61P 37/02 424/773 |
| 2005/0244511 A1 | * | 11/2005 | Laurie .................... | A61K 33/24 424/641 |

OTHER PUBLICATIONS

Geissinger et al (Canadian Journal of Comparative Medicine, 1981, vol. 45, pp. 97-102) (Year: 1981).*
Luo et al. (Environmental Pollution, 2006, vol. 144, pp. 862-871) (Year: 2006).
wps.prenhall.com website (Factors that affect solubility, chapters 13 and 17), downloaded 2017 (Year: 2017).

* cited by examiner

*Primary Examiner* — Mark V Stevens
(74) *Attorney, Agent, or Firm* — Finnegan, Henderson, Farabow, Garrett & Dunner, LLP

(57) ABSTRACT

A trace element solution comprises at least the following metals: zinc; manganese; selenium; and copper; and which comprises a concentration of the metals of at least 90 mg/ml. The solution may comprise the following concentrations: at least 60 mg/ml zinc; at least 10 mg/ml manganese; at least 5 mg/ml selenium; and at least 15 mg/ml copper. The solution may comprise chromium, iodine and chromium.

15 Claims, No Drawings

TRACE ELEMENTS

This application is a continuation of U.S. application Ser. No. 16/429,685, filed Jun. 3, 2019, which is a continuation of U.S. application Ser. No. 15/968,866, filed May 2, 2018, now U.S. Pat. No. 10,350,241, issued Jul. 16, 2019, which is a continuation of abandoned U.S. application Ser. No. 15/660,439, filed Jul. 26, 2017, which is a division of U.S. application Ser. No. 13/130,336, filed Aug. 4, 2011, now U.S. Pat. No. 9,750,764, issued Sep. 5, 2017, which is a national filing under 35 U.S.C. § 371 of International Application No. PCT/IB09/55402, filed Nov. 30, 2009, which claims priority of South African Application No. 200810426, filed Dec. 9, 2008. The contents of these applications are each incorporated herein by reference.

FIELD OF INVENTION

The present invention relates to trace elements.

BACKGROUND TO INVENTION

It has been found that there is a deficiency of certain trace elements in pastures for livestock in particular areas around the world. Various suggestions have been made to provide the required trace elements to such animals. Different chemical compounds and complexes have been investigated for applying the trace elements by way of licks, drenches or injections.

In general the problem with injectable solutions is that the concentrations of the minerals in the solutions is too low. This means that relatively large quantities have to be injected, which in turn causes tissue damage and also abscesses at the site of injection. Furthermore, it is generally the case that different trace elements seldomly are individually sufficient. This means that two or more trace element solutions have to be provided by way of separate injections.

ZA 1982/6778 (Laurie) discloses a trace element solution and a method of providing the trace elements to livestock. These trace element solution include ethylene diamino tetra acetic acid complex of the required mineral in suitable quantities. However, the trace element solution includes no selenium or selenite compound.

In the specification and claims the expression EDTA refers to ethylene diaminotetraacetic acid ($C_{10}H_{16}O_8N_2$ or $(HO_2CH_2C)_2NCH_2CH_2N-(CH_2CO_2H)_2$).

U.S. Pat. No. 4,335,116 (Howard) discloses mineral-containing therapeutic compositions containing EDTA complexes of trace elements. Notably, U.S. Pat. No. 4,335,116 utilises tetra-sodium EDTA, a selenium glycine complex, and metal chlorides for the preparation of the EDTA complexes. Unfortunately, the chloride ions cause contamination and each complex solution is to be made individually. Furthermore, overnight time is required for complexing and heating up afterward to speed up the process, requires extra apparatus. If mixtures are required, the individual solutions are to be blended. If various concentrations as well as compositions are to be made, it can only be done in a cumbersome way, requiring extra apparatus. A further problem arises when mixtures of high concentration are needed. In certain cases it would be impossible to deliver them, because mixing is always accompanied by dilution. The maximum concentration achieved with this method was 13.5 mg/ml.

U.S. Pat. No. 6,638,539 (Laurie et al) discloses a method of preparing a trace element solution, which includes the steps of providing at least one EDTA-complex, of providing a sodium selenite solution, and of combining the EDTA-complexes and the sodium selenite solution. However, the method enables production of a trace element solution of only about 55 mg/ml.

U.S. Pat. No. 7,285,292 (Laurie et al) discloses a trace element solution, which comprises at least one metal selected from the group comprising selenium, copper, zinc, manganese and chromium and which comprises a concentration of the metal(s) of at least 60 mg/ml. The solution further comprises at least one compound selected from the group comprising iodine, potassium iodide, sodium iodide, iron, iron chloride, zinc oxide, manganese sulphate, sodium selenite, copper carbonate, sodium carbonate, anhydrous disodium EDTA and sodium hydroxide. The trace element solution is prepared by a method consisting essentially of the steps of preparing a $MnCO_3$ mixture in a container; adding an EDTA/NaOH mixture to the container and subsequently adding at least one metal compound; and adding $Na_2SeO_3$ to the container to obtain the trace element solution. The method also comprises the step of adding $CrCl_3.6H_2O$ to the trace element solution.

Unfortunately the known solutions and methods therefore cannot provide solutions with suitable composition with high enough concentrations and sufficient ratios and sufficient concentrations of the various metals.

It is an object of the invention to suggest methods and means for overcoming these problems.

SUMMARY OF INVENTION

According to the invention, a trace element solution, which comprises at least the following metals:
 (a) zinc;
 (b) manganese;
 (c) selenium; and
 (d) copper,
and which comprises a concentration of the metals of at least 90 mg/ml.

Also according to the invention, a method of preparing a trace element solution comprising at least one metal selected from the group comprising zinc, manganese, selenium, and copper and comprising a concentration of the metals of at least 90 mg/ml, said method consisting essentially of the steps of:
 (a) heating water;
 (b) adding manganese carbonate to the water;
 (c) adding zinc oxide to the water; and
 (d) adding copper carbonate to the water to form a liquid mixture;
 (e) adding a dry mixture comprising EDTA and/or EDDS and NaOH to the liquid mixture; and
 (f) adding $Na_2SeO_3$ to form the trace element solution.

Yet further according to the invention, a trace element solution as prepared by the method as described herein.

Yet further according to the invention, a method of providing trace elements to animals, such as livestock, which comprises the steps of preparing a trace element solution as described herein and of providing the solution in a suitable quantity to an animal.

The method of preparing a trace element solution may be a continuous batch process.

The solution may comprise the following concentrations:
 (a) at least 60 mg/ml zinc;
 (b) at least 10 mg/ml manganese;
 (c) at least 5 mg/ml selenium; and
 (d) at least 15 mg/ml copper.

The solution may comprise chromium.

The solution may comprise iodine.

The solution may comprise at least 5 mg/ml chromium.

The solution may comprise at least 50-300 mg/ml iodine.

The ratio of zinc to manganese may be at least 2:1

The ratio of zinc to manganese may be at least 4:1

The ratio of zinc to copper may be at least 2:1 or 4:1

The ratio of zinc to selenium may be at least 4:1 or 12:1

The solution may comprise at least one compound selected from the group comprising chromium, iron, iodine, potassium iodide, sodium iodide, iron chloride, zinc oxide, manganese sulphate, manganese carbonate, sodium selenate, sodium selenite, copper carbonate, sodium carbonate, anhydrous disodium EDTA and sodium hydroxide.

At least one of the metal(s) may be provided in the form of an EDTA complex and/or an EDDS complex.

The EDTA source may be EDTA acid, disodium EDTA, tetra-sodium EDTA, calcium EDTA, potassium EDTA and/or any other EDTA source.

The solution may comprise chloro-cresol and/or benzyl alcohol as preservative.

The solution may be an injectable solution.

The solution may be a drenchable solution.

Step (a) may heat the water to 70 degrees Celsius.

The adding in step (e) may occur slowly to prevent excessive frothing.

The solution may be a clear blue solution.

The temperature of the solution may reach 100 degrees Celsius.

The solution may be allowed to cool.

The solution may after cooling have a temperature of 50 degrees Celsius.

Chloro-cresol may be added to the solution and stirred until dissolved.

The pH of the solution may be adjusted.

Water may be added to the solution.

The method may comprise the step of adding $CrCl_3 \cdot 6H_2O$ to the trace element solution.

The method may comprise the step of adjusting the pH of the trace element solution to 6.0 to 8.0

The method may comprise the step of adjusting the pH of the trace element solution by adding at least one compound selected from the group comprising NaOH and EDTA.

The trace element solution may be diluted.

The temperature of the $MnCO_3$ mixture may be at least 60 degrees Celsius.

Water having a temperature of at least 70 degrees Celsius may be added to the $MnCO_3$ mixture.

The addition of the EDTA/NaOH mixture may occur gradually with small quantities.

The method may comprise the step of cooling the trace element solution prior to addition of the $Na_2SeO_3$.

The $MnCO_3$ mixture may be obtained directly and/or prepared by mixing $MnSO_4$ and $Na_2CO_3$.

The metal compound may be selected from the group comprising ZnO, $CuCO_3$, $Na_2CO3$, $MnSO_4$ and $FeCl_3$.

The metal compound may be selected from the group comprising metal oxides, metal hydroxides and metal carbonates.

DESCRIPTION EXAMPLE

The invention will now be described by way of an example of injectable solutions in accordance with the invention.

The example relates to a method to prepare a trace element solution predominantly to be used for cattle and includes the mineral elements zinc, manganese, selenium and copper.

The method enables preparation of 25 litres of the solution containing at least 60 mg Zn, 10 mg Mn, 5 mg Se, and 15 mg Cu per ml.

In a 25 litre plastic container, water is heated to a temperature of 70 degrees Celsius so that the process can proceed at a temperature of at least 60 degrees Celsius.

0.556 Kilogram of manganese carbonate is added to the heated water whilst mixing.

1.890 Kilogram of zinc oxide is added to the mixture.

0.700 Kilogram of copper carbonate is added to the mixture slowly to form a liquid mixture.

In a separate container 10.17 kilogram EDTA and 2.70 kilogram of NaOH are mixed to form a dry mixture.

The dry mixture is slowly added to the liquid mixture to prevent excessive frothing and allow the reaction to complete and to leave a clear blue solution.

The temperature of the solution may reach 100 degrees Celsius and is allowed to cool to 50 degrees Celsius.

26.25 g of Chloro-cresol is added to the solution and is stirred until dissolved.

The solution is then cooled to room temperature.

The recorded pH of the solution is now 4.656.

0.303 Kilogram of $Na_2SeO_3$ is added.

The recorded pH of the solution is now 5.115.

The pH is adjusted to 6.860 by adding a 50% NaOH solution.

The solution is now diluted with water to obtain the required weight, namely 1.300 kg/l.

The resultant trace element solution has a composition as follows:

(a) 60 mg/ml of zinc;
(b) 10 mg/ml manganese;
(c) 5 mg/ml selenium; and
(d) 15 mg/ml copper.

The invention therefore provides a trace element solution which is tissue friendly, i.e. is not damaging or irritant to the tissue of animals and which comprises zinc, manganese, selenium and copper and at a concentration of the metals of at least 90 mg/ml.

The trace elements in solution are in a scientifically formulated ratio according to the post-absorption requirements of the animals.

As an example the trace element solution comprises (a) at least 60 mg/ml of zinc;
(b) at least 10 mg/ml manganese;
(c) at least 5 mg/ml selenium; and
(d) at least 15 mg/ml copper.

The solution may furthermore comprise at least 5 mg/ml chromium and at least 50-300 mg/ml iodine.

The method of preparing a trace element solution in accordance with the invention thus enables the production of a solution comprising an adequate trace mineral concentration so that a 5 to 10 millilitre injection can make a significant impact on the trace mineral status of the animal and an injection is provided at a rate of between 1 ml per 50 kg bodyweight (BW) and 1 ml per 100 kg BW, i.e. a practically applicable injectable supplement and a product that can improve the trace mineral status of an animal is provided. This is important as livestock producers will only inject livestock if a real benefit can be demonstrated. The subcutaneous injection is the preferred route to minimize tissue damage, but intra-muscular injection can also be used.

The invention claimed is:

1. A method of improving the trace mineral status of a livestock animal, comprising injecting a trace element aqueous injectable solution into a livestock animal in need thereof, wherein said trace element aqueous injectable solution comprises zinc, copper, and at least one other trace element, wherein the concentration of zinc ranges from 60 mg/ml up to a concentration that, in combination with said copper and at least one other trace element, preserves the suitability for injection of the trace element aqueous injectable solution.

2. The method of improving the trace mineral status of a livestock animal according to claim 1, wherein the solution further comprises manganese and wherein the concentration of manganese in combination with the concentration of said zinc, copper, and at least one other trace element, preserves the suitability for injection of the trace element aqueous injectable solution.

3. The method of improving the trace mineral status of a livestock animal according to claim 1, wherein the concentration of copper ranges from 5 mg/ml up to a concentration that, in combination with the concentration of said zinc and at least one other trace element, preserves the suitability for injection of the trace element aqueous injectable solution.

4. The method of improving the trace mineral status of a livestock animal according to claim 1, wherein the solution further comprises iodine, and wherein the concentration of iodine in combination with the concentration of said zinc, copper, and at least one other trace element, preserves the suitability for injection of the trace element aqueous injectable solution.

5. The method of improving the trace mineral status of a livestock animal according to claim 4, wherein the concentration of iodine ranges from 50 mg/ml up to 300 mg/ml, and wherein the concentration of iodine in combination with the concentration of said zinc, copper, and at least one other trace element, preserves the suitability for injection of the trace element aqueous injectable solution.

6. The method of improving the trace mineral status of a livestock animal according to claim 1, wherein the solution further comprises chromium, wherein the concentration of chromium in combination with the concentration of said zinc, copper, and at least one other trace element, preserves the suitability for injection of the trace element aqueous injectable solution.

7. The method of improving the trace mineral status of a livestock animal according to claim 6, wherein the concentration of chromium ranges from 5 mg/ml up to a concentration that, in combination with the concentration of said zinc, copper, and at least one other trace element, preserves the suitability for injection of the trace element aqueous injectable solution.

8. The method of improving the trace mineral status of a livestock animal according to claim 4, wherein the solution further comprises chromium, wherein the concentration of said chromium in combination with the concentration of said zinc, copper, iodine, and at least one other trace element, preserves the suitability for injection of the trace element aqueous injectable solution.

9. The method of improving the trace mineral status of a livestock animal according to claim 2, wherein the concentration of copper ranges from 5 mg/ml up to a concentration that, in combination with the concentration of said zinc, manganese, and at least one other trace element, preserves the suitability for injection of the trace element aqueous injectable solution.

10. The method of improving the trace mineral status of a livestock animal according to claim 2, wherein the concentration of manganese ranges from 10 mg/ml up to a concentration that, in combination with the concentration of said zinc, copper, and at least one other trace element, preserves the suitability for injection of the trace element aqueous injectable solution.

11. The method of improving the trace mineral status of a livestock animal according to claim 2, wherein the solution further comprises iodine, wherein the concentration of iodine in combination with the concentration of said zinc, copper, manganese, and at least one other trace element, preserves the suitability for injection of the trace element aqueous injectable solution.

12. The method of improving the trace mineral status of a livestock animal according to claim 11, wherein the concentration of iodine ranges from 50 mg/ml up to 300 mg/ml, and wherein the concentration of iodine combination with the concentration of said zinc, copper, manganese, and at least one other trace element, preserves the suitability for injection of the trace element aqueous injectable solution.

13. The method of improving the trace mineral status of a livestock animal according to claim 2, wherein the solution further comprises chromium, wherein the concentration of chromium in combination with the concentration of said zinc, copper, manganese, and at least one other trace element, preserves the suitability for injection of the trace element aqueous injectable solutions.

14. The method of improving the trace mineral status of a livestock animal according to claim 13, wherein the concentration of chromium ranges from 5 mg/ml up to a concentration that, in combination with the concentration of said zinc, copper, manganese, and at least one other trace element, preserves the suitability for injection of the trace element aqueous injectable solution.

15. The method of improving the trace mineral status of a livestock animal according to claim 11, wherein the solution further comprises chromium, wherein the concentration of said chromium in combination with the concentration of said zinc, copper, manganese, iodine, and at least one other trace element, preserves the suitability for injection of the trace element aqueous injectable solution.

* * * * *